United States Patent [19]

Chern

[11] Patent Number: 5,214,379
[45] Date of Patent: May 25, 1993

[54] METHOD AND APPARATUS FOR DEFLECTION MEASUREMENTS USING EDDY CURRENT EFFECTS

[75] Inventor: Engmin J. Chern, Columbia, Md.

[73] Assignee: The United States of America as represented by the Administrator of the National Aeronautics and Space Administration, Washington, D.C.

[21] Appl. No.: 904,308

[22] Filed: Jun. 25, 1992

[51] Int. Cl.⁵ ............... G01B 7/28; G01B 5/20; G01N 27/72
[52] U.S. Cl. ............... 324/220; 33/542; 324/207.16; 324/262
[58] Field of Search ............ 324/207.11, 207.12, 324/207.13, 207.15, 207.16, 207.17, 207.18, 207.19, 207.22, 207.23, 207.25, 219, 220, 221, 262; 33/501.6, 542, 543, 544; 165/11.2

[56] References Cited

U.S. PATENT DOCUMENTS

| | | | |
|---|---|---|---|
| 2,602,660 | 7/1952 | Shannon | 324/207.12 X |
| 3,461,400 | 8/1969 | Koda | 324/207.16 X |
| 4,555,855 | 12/1985 | Golinelli et al. | 324/207.16 X |
| 4,663,589 | 5/1987 | Fiori, Jr. | 324/207.16 |
| 4,719,419 | 1/1988 | Dawley . | |
| 4,868,498 | 9/1989 | Lusinchi et al. . | |
| 4,876,506 | 10/1989 | Brown et al. | 324/220 |
| 4,912,406 | 3/1990 | Chollet et al. | 324/207.23 |
| 4,914,390 | 4/1990 | Orlicki et al. . | |
| 5,059,904 | 10/1991 | Mazzone et al. . | |
| 5,083,084 | 1/1992 | Bauer et al. . | |

FOREIGN PATENT DOCUMENTS 1232937 5/1986 U.S.S.R. .
2240184 7/1991 United Kingdom ........... 324/207.25

Primary Examiner—Gerard R. Strecker
Attorney, Agent, or Firm—Paul S. Clohan, Jr.; R. Dennis Marchant; Guy M. Miller

[57] ABSTRACT

A method and apparatus for inserting and moving a sensing assembly with a mechanical positioning assembly to a desired remote location of a surface of a specimen under test and measuring angle and/or deflection by sensing the change in the impedance of at least one sensor coil located in a base plate which has a rotatable conductive plate pivotally mounted thereon so as to uncover the sensor coil(s) whose impedance changes as a function of deflection away from the center line of the base plate in response to the movement of the rotator plate when contacting the surface of the specimen under test. The apparatus includes the combination of a system controller, a sensing assembly, an eddy current impedance measuring apparatus, and a mechanical positioning assembly driven by the impedance measuring apparatus to position the sensing assembly at a desired location of the specimen.

19 Claims, 4 Drawing Sheets

METHOD AND APPARATUS FOR DEFLECTION MEASUREMENTS USING EDDY CURRENT EFFECTS

ORIGIN OF THE INVENTION

The invention described herein was made by an employee of the United States Government, and may be manufactured and used by or for the Government for governmental purposes without the payment of any royalties thereon or therefor.

BACKGROUND OF THE INVENTION

This invention relates generally to eddy current testing methods and apparatus, and more particularly to an eddy current type of method and apparatus for measuring deflection profiles, radius of curvature, and the like.

Angle, displacement and deflection measurements based on dimensional, electromechanical, gravitation and other principles are generally known and heretofore have used a variety of apparatus such as dowel pins, machine gauges, capacitance devices and linear variable differential transformers.

Eddy current type surface probes are also known. In such apparatus, eddy currents are produced in an electrically conductive test piece by a coil through which an alternating current flows, and as a result of the eddy currents produced therein, impedance of the coil and the voltage applied to the coil are changed and thus the measurement of a particular characteristic of the surface is determined by a measured change in impedance of the sensor coil. However, state of the art angle and displacement measuring devices are normally operator dependent and typically require direct line of sight or line of measurement accessibility of the specimen and thus cannot be used in the interior of elongated closed structures such as curved metal pipes or tubes.

SUMMARY

It is therefore a primary object of the present invention to provide an improvement in eddy current testing methods and apparatus.

It is a further object of the invention to provide an improved eddy current method and apparatus for measuring deflection, profile and radius of curvature of an object.

It is another object of the invention to provide improvement in eddy current testing method and apparatus for making angle, displacement and deflection measurements on a relatively inaccessible surface of a specimen under test.

And it is yet another object of the invention to provide an improvement in eddy current testing methods and apparatus for making deflection measurements on the interior of a tube accurately and reliably without operator intervention.

Briefly, the foregoing and other objects are achieved by inserting and moving a sensing assembly with a mechanical positioner to a desired remote location of a surface of a specimen under test and measuring angle and/or deflection by sensing the change in the impedance of at least one sensor coil located in a base plate which has a rotatable sensor plate pivotally mounted thereon so as to uncover the sensor coil(s) whose impedance changes as a function of deflection away from the center line of the base plate in response to means mounted on the rotator plate contacting the surface of the specimen under test. The apparatus involved includes a system controller, a sensing assembly, an eddy current impedance measuring apparatus, and a mechanical probe pusher or crawler driven by the position controller to position the sensing assembly at a desired location of the specimen.

BRIEF DESCRIPTION OF THE DRAWINGS

The following detailed description will be more readily understood when considered together with the accompanying drawings wherein.

DETAILED DESCRIPTION OF THE INVENTION

Figure 1:
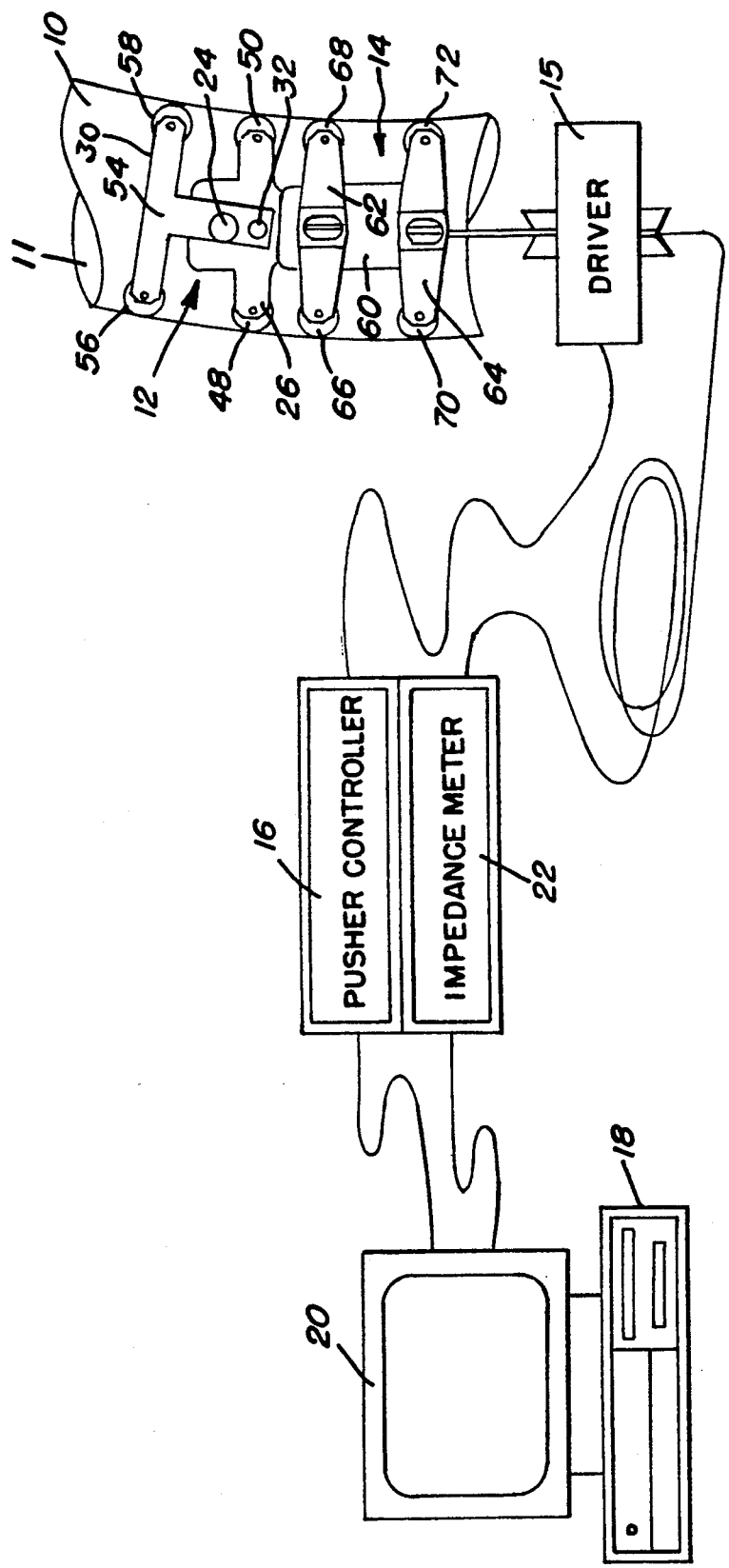
FIG. 1 is an electrical-mechanical block diagram of a preferred embodiment of apparatus for implementing the subject invention.

Referring now to the drawings and more particularly to FIG. 1, the block diagram shown thereat is generally illustrative of a system, in accordance with the subject invention, for making deflection angle and displacement measurements at a remote location, for example, within a length of pipe or tubing 10 utilizing an eddy current testing technique, the general principles of which are well known. The system utilizes an eddy current deflectionmeasuring assembly 12 which is inserted into the tube 10 and mechanically driven to a desired location without operator intervention by means of a probe pusher assembly 14 which can be in the form of a crawler which is propelled by a driver device 15 controlled in response to positional control signals received from an external controller 16 coupled to a digital computer 18 having a video (CRT) display unit 20 associated therewith. The computer 18 is used primarily for mechanical control, data acquisition, processing and analysis. When desirable, the crawler 14 and the driver 15 can be integrated into a single unit.

The eddy current sensing assembly 12 is coupled to the computer 18 through an impedance meter 22 for measuring the impedance change in at least one eddy current sensing coil 24 whose electrical impedance characteristic changes in response to changes in eddy currents induced by the coil 24 when partially covered by the electrical conductive plate 30 in a corresponding deflected region of the tube 10 at the location of the sensing assembly 12.

Figure 2:
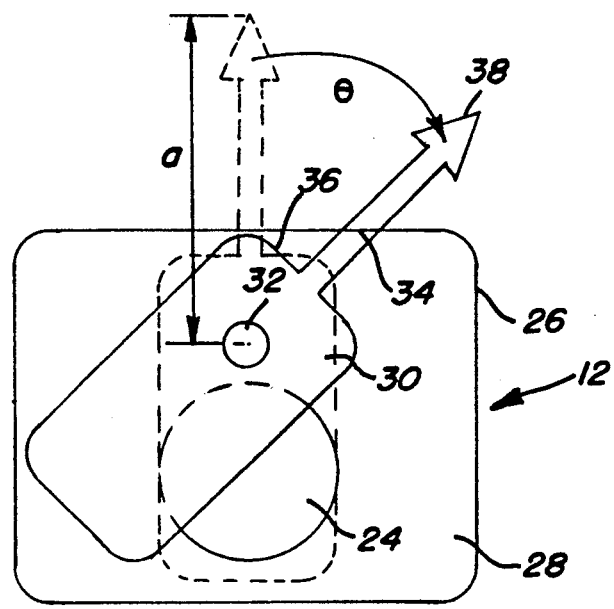
FIG. 2 a top elevational view of a relatively simple single coil eddy current deflectometer which can be used to implement the subject invention.

In its simplest and most generalized form, the sensor assembly 12 can be configured as shown in FIG. 2, and is comprised of, for example, an electrically nonconductive base plate 26 of generally rectangular configuration which is mounted on or connected to a pusher unit, not shown. Further, the base plate 26 includes a single eddy current sensor coil 24 located toward one end thereof. The sensor coil 24, moreover, is circular in transverse cross section and has a generally flat upper surface which is at least flush with or below the top surface 28 of the base plate 26 so that a rotatable conductive top plate 30 can be pivotally mounted thereon by means of a pivot pin 32 or the like. The upper plate 30 is also of generally rectangular configuration and having a length (including pointer element 34) at least equal to that of the base plate 26 but is reduced in width relative thereto. However, the width dimension of the upper plate 30 is at least equal to the diameter of the sensor coil 24 so that it can completely cover the sensor coil 24 when oriented with a zero deflection angle θ as shown by the phantom lines. In this position, the lower and upper plates 26 and 30 are mutually aligned.

The upper plate 30, moreover, includes a pointer element 34 which extends longitudinally outwardly from the front edge 36 of the plate 30 for a predetermined length "a" and having a relatively sharp tip 38 at the far end which is used to contact a surface of a specimen under test, not shown, which operates to deflect the pointer 34 including the top plate 30 and thus expose a surface portion of the sensor coil 24 as a function of deflection angle $\theta$. A change in the impedance of the sensor coil 24 results depending upon the amount of the sensor coil 24 which is exposed. This provides a means for providing angular measurement.

Figure 3:
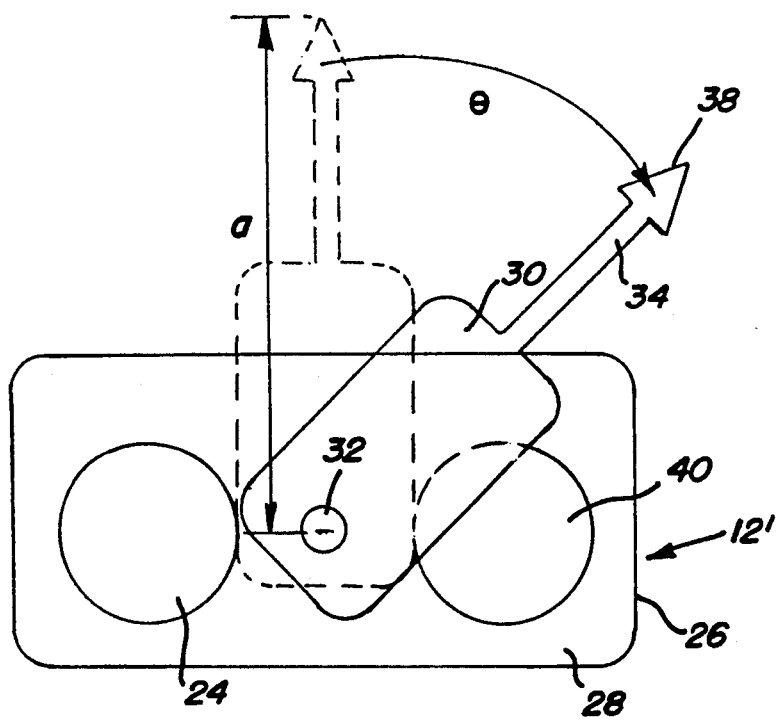
FIG. 3 is a top planar view of a dual sensor coil eddy current deflectometer similar to that shown in FIG. 2.

A variation of this type of the eddy current sensing assembly is shown in FIG. 3 and comprises the sensor assembly 12'. It differs from the sensor assembly 12 shown in FIG. 2 by the inclusion of a second coil 40 in the base plate 26 and which is located symmetrically opposite the sensor coil 24 and between the top plate 30 when in the position as depicted by the phantom lines, i.e. $\theta = 0°$. As a result of the inclusion of the second coil 40, the width of the bottom plate 26 must necessarily be widened to accommodate both coils 24 and 40 being mounted therein. In all other respects, the two sensing assemblies 12 and 12' are identical. The single coil arrangement 12 provides an absolute eddy current sensing configuration, whereas the two coil arrangement shown in FIG. 3 can provide a differential arrangement for providing a relationship between signal amplitude and deflection as well as providing directional information of the deflection (±).

While the design of the coils 24 and 40 are shown being circular in configuration, other designs involving coil shape and size can be utilized depending upon the range, sensitivity and accuracy required. Also, the sensing assemblies 12 and 12' can be designed to accommodate the specific specimen geometries being measured. Also, when desired, mechanical attachments can also be designed and incorporated with the sensing assembly.

Figure 4:
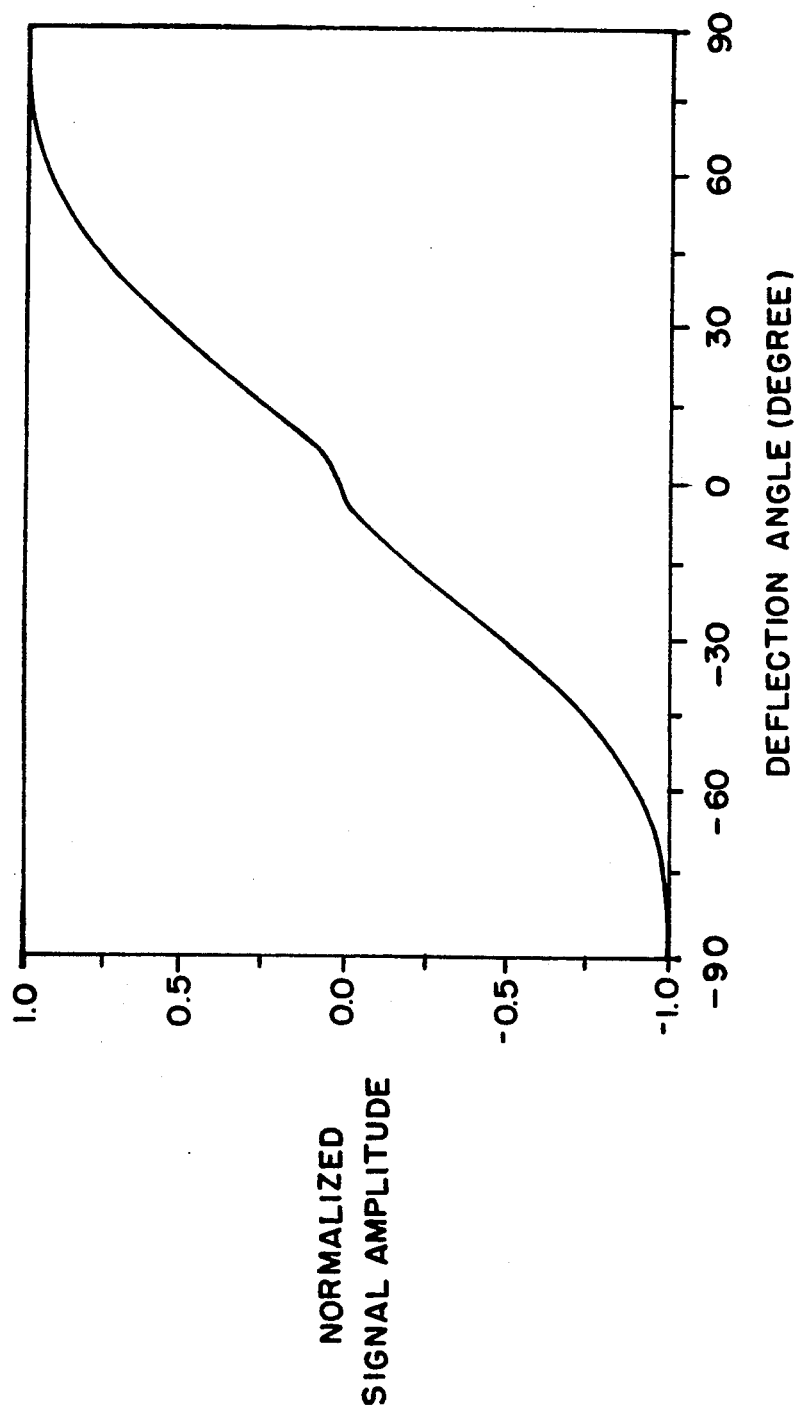
FIG. 4 is a characteristic curve illustrative of eddy current signal amplitude as a function of deflection angle in an current deflectometer.

Signal amplitude as a function of deflection angle $\theta$ is shown in FIG. 4. With the signal amplitude being a normalized value, the graph as depicted in FIG. 4 represents a calibration curve for the system by measuring the eddy current response with respect to ± angle $\theta$ and can be obtained empirically since displacement is directly proportional to distance "a" times the sine of any $\theta$ (FIG. 3).

Figure 6:
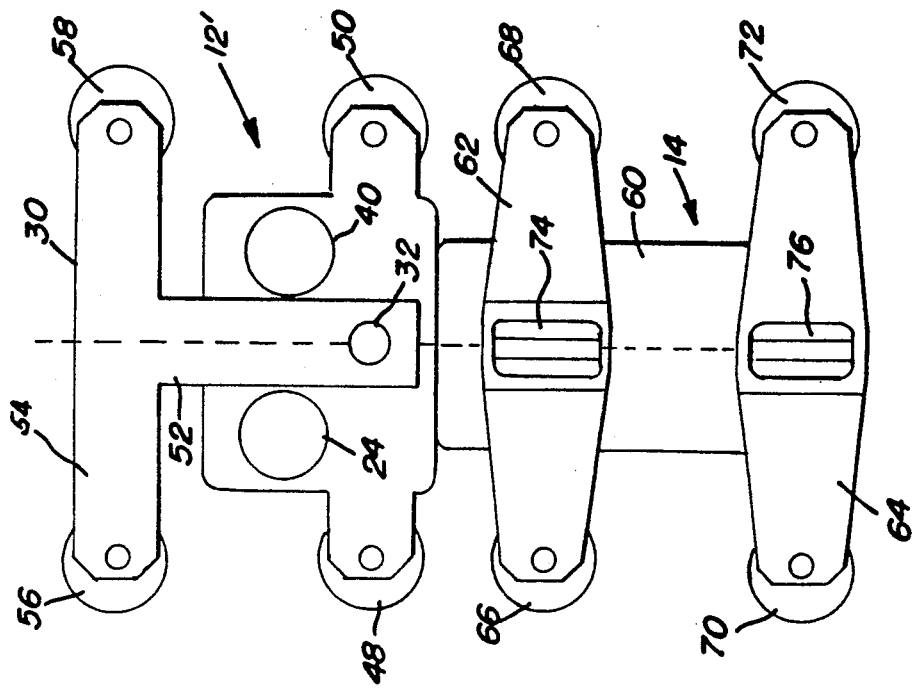
FIG. 6 is a top elevational view of a double coil configuration of the deflectometer shown in FIG. 5.
Figure 5:
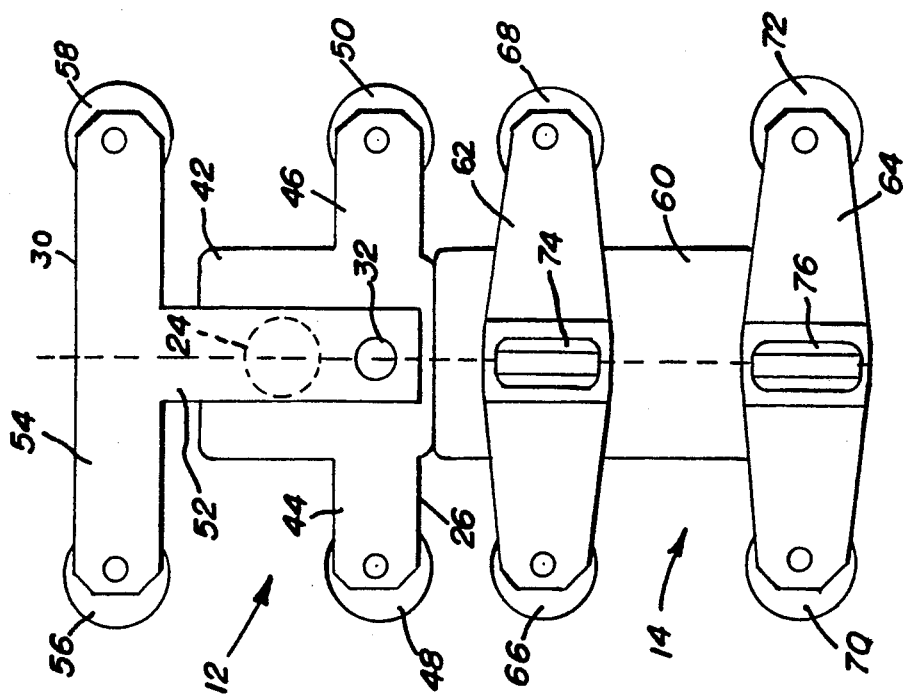
FIG. 5 is a top elevational view of a single coil eddy current deflectometer particularly adapted for use in connection with a pipe or tube angle measurement shown in FIG. 1.

This now leads to the preferred embodiments of the invention which are shown in FIGS. 5 and 6. Referring first to FIG. 5, shown thereat is a single coil configuration for pipe/tube deflection measurement and which is also shown in FIG. 1. The sensor assembly 12 is now comprised of a T-shaped assembly whose base plate 26 includes not only a generally rectangular body portion 42, but a pair of outwardly extending arm members 44 and 46 to which is attached a pair of rollers or wheels 48 and 50. The rollers 48 and 50 are adapted to contact the inside surface 11 (FIG. 1) of a tube or pipe 10 and having a top plate 30 including an elongated body portion 52 which is secured to the base plate 26 by means of the pivot 32 which is now located tandem to an eddy current sensing coil 24 and in line with rollers 48 and 50. The width of the body portion 52 is at least equal to the diameter of the cross sectional dimension of the sensing coil 24 and terminates in a forwardly located cross member 54 which has a pair of rollers 56 and 58 attached to the outward extremities thereof. Thus as the sensing assembly 12 is moved through the pipe 10, the front rollers 56 and 58 follow the inside surface 11 of the pipe and cause the top plate member 30 to pivot either to the left or right and uncover a portion of the sensing coil 24 in the same manner as was described with respect to the sensing coil configuration shown in FIG. 2.

The crawler assembly 14 is shown comprised of a body member 60 which is generally of the same length as the combined length of the sensing assembly 12 and having forward and aft cross members 62 and 64 having pairs of rollers 66, 68 and 70, 72 attached thereto in the same fashion as the sensing assembly roller members 48 ... 58. The crawler assembly 14 is propelled forward and backward by the driver 15 shown in FIG. 1. Both of the cross arm members 62 and 64 additionally include upward extending spacer members 74 and 76 for stabilizing the crawler assembly during its travel in the tube or pipe 10.

Referring now to FIG. 6, shown thereat is a double coil configuration similar to that shown in FIG. 3 but comprising the components shown in FIG. 5. However, now a second sensing coil 40 is added with both coils 24 and 40 being located symmetrically on either side of the forwardly extending body member 52 of the upper plate 30. In operation, as the sensing assembly 12' traverses a curved portion of the tube or pipe 10, the forwardly extending body portion 52 of the top plate member 30 will cover a portion of one of the sensing coils, depending upon the radius of curvature of the tube portion being traversed. Thus if the top plate 30 pivots to the right, a portion of sensor coil 40 will be covered, while if the top plate 30 pivots to the left, that portion of the sensor coil 24 will be covered in the same fashion as the configuration shown in FIG. 3.

The apparatus according to the subject invention is fully automated and is particularly adapted for remote sensing and because of its unique configuration, is stable for relatively long periods of time and does not require line of sight or line of measurement of the specimen.

Having thus shown and described what is at present considered to be the preferred embodiments of the invention, it should be noted that the same has been made by way of illustration and not limitation. Accordingly, all modifications, alterations and changes coming within the spirit and scope of the invention are herein meant to be included.

I claim:

1. A method of automatic eddy current testing for determining angular deflection at a predetermined location of a specimen, comprising the steps of:
    (a) attaching a sensing assembly including at least one eddy current sensing coil to a propulsion device, said sensing assembly including means adapted to cover and uncover said eddy current sensing coil for varying the amplitude of an output signal from said eddy current sensing coil as a function of the deflection of said means for varying the amplitude, said means contacting the specimen at said predetermined location thereby uncovering said eddy current sensing coil;

(b) positioning the sensing assembly in the vicinity of said predetermined location;

(c) generating eddy currents in the specimen by said eddy current sensing coil at said predetermined location and measuring the amplitude of said output signal;

(d) moving the sensing assembly under remote control in a predetermined travel path at said predetermined location;

(e) sensing the amplitude change of said output signal resulting from said step of moving; and (f) determining said angular deflection as a function of said amplitude change.

2. The method of claim 1 wherein said step (b) of positioning the sensing assembly comprises positioning by remote control.

3. The method of claim 1 wherein said step (f) of determining a measure of angular deflection comprises generating a deflection profile of the specimen from repetitive measurements of said amplitude change at said location.

4. The method of claim 1 wherein said step (b) of positioning comprises positioning the sensor assembly with a mechanical propulsion assembly.

5. The method of claim 1 wherein said sensing assembly includes a pair of eddy current sensing coils and said step (e) of sensing amplitude change comprises measuring differentially amplitude change as a function of output signals from said pair of sensing coils.

6. The method of claim 1 wherein said step (f) of determining said angular deflection comprises determining a radius of curvature of said specimen at said predetermined location from a three point data set of said output signals.

7. An eddy current for making angular measurements of a specimen without human intervention, comprising:

(a) a system controller generating signals for effecting mechanical control of the system and controlling data acquisition, processing and analysis;

(b) an eddy current sensing assembly including a base member having at least one eddy current sensing coil located thereon, and a rotatable member pivotally mounted on the base member for covering and uncovering the sensing coil as a function of the mutual rotation of said base member and said rotatable member, and further having means secured to the rotatable member for contacting a surface of the specimen thereby providing rotation of said rotatable member;

(c) a mechanical propulsion assembly attached to the sensing assembly for locating and moving the sensing assembly at a predetermined location relative to the specimen;

(d) positioning assembly control means responsive to signals from said system controller for controlling the movement of the propulsion assembly;

(e) impedance measuring means controlled by signals generated by said system controller and being coupled to said sensing coil for measuring impedance change in said sensing coil whose electrical impedance characteristics change in response to changes in eddy currents generated by said coil as a function of said mutual rotation; and (f) means coupled to said system controller for generating an indication of said mutual rotation from said impedance change in said sensing coil so as to provide an angular measurement at said location of said specimen.

8. The system of claim 7 wherein said means for contacting the surface of the specimen comprises means extending outward from a forward portion of said rotatable member.

9. The system of claim 7 wherein said sensing coil is generally circular in cross section, said circular cross section facing said rotatable member.

10. The system of claim 7 wherein said at least one sensing coil is located so as to be substantially covered by said rotatable member when said base member and said rotatable member are mutually aligned along a common central axis.

11. The system of claim 10 and additionally including at least one other eddy current sensing coil located on said base member so as to be substantially uncovered by said rotatable member when said base member and said rotatable member are mutually aligned along said common central axis.

12. The system of claim 7 wherein said system controller comprises a digital apparatus and wherein said eddy current sensing assembly includes a pair of differentially operating eddy current sensing coils.

13. The system of claim 12 wherein said pair of sensing coils have generally circular cross sections facing said rotatable member.

14. The system of claim 13 wherein one coil of said pair of sensing coils is offset to one side of a central longitudinal axis common to both said base member and said rotatable member, and wherein the other coil of said pair of sensing coils is also offset from said central axis and symmetric with said one coil.

15. The system of claim 14 wherein said one coil is covered and said other coil is uncovered when said rotatable member and base member are mutually aligned along said central longitudinal axis.

16. The system of claim 15 wherein said pair of sensing coils are of substantially the same size.

17. The system of claim 15 wherein said means for contacting said surface of the specimen comprises a relatively thin elongated member located along said central longitudinal axis and having a pointed end for contacting the surface of said specimen and rotating said rotatable member.

18. The system of claim 15 wherein said rotatable member comprises a T-shaped member including a forwardly located area member having roller means secured to the outer ends thereof.

19. The system of claim 17 wherein said base member includes a body portion and a pair of arm portions extending outwardly from said body portion and having roller means secured to the outer ends of said arm portions.

* * * * *